United States Patent [19]

Ching

[11] 4,307,240

[45] Dec. 22, 1981

[54] ALKOXYSILANES AND METHOD FOR MAKING

[75] Inventor: Ta-Yen Ching, Schenectady, N.Y.

[73] Assignee: General Electric Company, Schenectady, N.Y.

[21] Appl. No.: 154,626

[22] Filed: May 30, 1980

[51] Int. Cl.$^3$ ............................ C07F 7/08; C07F 7/10; C07F 7/18

[52] U.S. Cl. .................................. 556/415; 556/416; 556/419; 556/440

[58] Field of Search ................ 556/415, 416, 419, 440

[56] References Cited

U.S. PATENT DOCUMENTS

| | | | |
|---|---|---|---|
| 2,775,605 | 12/1956 | de Benneville et al. | 556/415 |
| 2,872,435 | 2/1959 | Speier | 556/416 X |
| 3,584,026 | 6/1971 | Berger et al. | 556/416 |
| 3,646,091 | 2/1972 | Berger | 556/415 |
| 3,878,263 | 4/1975 | Martin | 556/416 X |
| 4,012,402 | 3/1977 | Buck | 556/416 |
| 4,051,161 | 9/1977 | Proskow | 260/448.8 R |
| 4,097,511 | 6/1978 | Berger | 556/415 X |
| 4,122,233 | 10/1978 | Proskow | 428/412 |
| 4,188,451 | 2/1980 | Humphrey | 428/331 |

*Primary Examiner*—Paul F. Shaver
*Attorney, Agent, or Firm*—William A. Teoli; James C. Davis, Jr.

[57] ABSTRACT

Alkoxysilylacrylamides, alkoxysilylacrylates and alkoxysilylbenzylidene malonates are provided and a method for making such materials. These alkoxysilanes have been found useful as UV stabilizers and as adhesion promoters when incorporated into silicone compositions useful as top coats for thermoplastic organic polymers.

7 Claims, No Drawings

ALKOXYSILANES AND METHOD FOR MAKING

CROSS REFERENCE TO RELATED APPLICATIONS

Reference is made to my copending applications Ser. No. 154,625, for Alkoxysilanes and Method for Making, and Ser. No. 154,623, and for Silicone Coating for Unprimed Plastic Substrates, Ser. No. 154,622 of Bruce A. Ashby and Siegfried H. Schroeter, for Ultraviolet Light Absorbing Agents and Articles Containing Same and Ser. No. 154,621 for Bruce A. Ashby, for Ultraviolet Light Absorbing Agents and Articles Containing Same. The aforementioned applications are filed May 30, 1980 and assigned to the same assignee as the present invention.

BACKGROUND OF THE INVENTION

The present invention relates to alkoxysilylacrylamides, alkoxysilylacrylates and alkoxysilylmalonates and method for making such materials.

Prior to the present invention, attempts were made to coat polycarbonate articles with polysilicic acid to impart improved mar resistance thereto. In Humphrey, U.S. Pat. No. 4,188,451, assigned to the same assignee as the present invention, a primer layer comprising a UV cured reaction product of a polyfunctional acrylic ester monomer and an organosilicon compound was used to improve adhesion of the polysilicic acid. The polysilicic acid was also combined with organic copolymers such as haloethylene-hydroxyvinyl ether copolymer to improve the adhesion of the polysilicic acid to the polycarbonate substrate as taught by Proskow, U.S. Pat. Nos. 4,051,161 and 4,122,233.

The present invention is based on the discovery, as taught in my copending application Ser. No. 15,623, for Silicone Coating for Unprimed Plastic Substrates, that certain alkoxysilanes including alkoxysilylacrylamides and alkoxysilyl acrylates, as defined hereinafter, can be added directly to polysilicic acid to produce valuable adherent silicone top-coat compositions. I have found that the silicone top-coat compositions containing the aforementioned alkoxysilylacrylamides in effective amounts by weight, can be applied directly onto polycarbonate substrates to produce mar resistant polycarbonate articles exhibiting superior resistance to UV degradation.

STATEMENT OF THE INVENTION

There is provided by the present invention, alkoxysilylacrylamides or alkoxysilylacrylates having the formula, $$(RO)_{4-a-b}Si(Y)_a \quad (R^1)_b \tag{1}$$

and alkoxysilylmalonates having the formula,

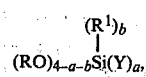
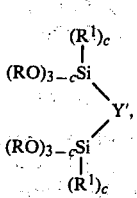
(2)

where Y is

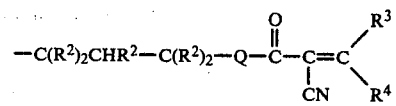

and Y' is

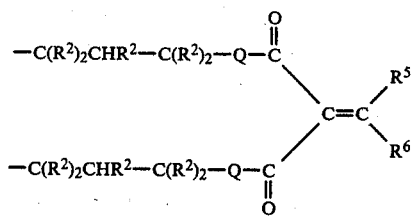

R is a $C_{(1-8)}$ alkyl radical, $R^1$ is selected from R, $C_{(6-13)}$ aryl radicals and halogenated derivatives thereof, $R^2$ is selected from hydrogen and R radicals, $R^3$ and $R^5$ are selected from $C_{(6-13)}$ aryl radical, $R^4$ and $R^6$ are selected from hydrogen, R and $R^3$ radicals, Q is selected from —O— and

a is an integer equal to 1 to 3 inclusive, b is a whole number equal to 0 to 2 inclusive and the sum of a+b is equal to 1 to 3 inclusive and c is a whole number equal to 0 to 2 inclusive.

Radicals included within R of formulas 1 and 2 are for example, methyl, ethyl, propyl, butyl, etc. Radicals which are included with $R^1$ are, for example in addition to R radicals phenyl, xylyl, tolyl, chlorophenyl, etc. Among the $C_{(6-13)}$ aryl radicals of $R^3$ and $R^5$, there are included the aforementioned aryl radicals of $R^1$.

Some of the alkoxysilanes which are included within formulas 1 and 2 are, for example,

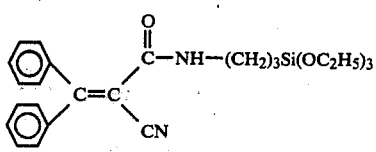

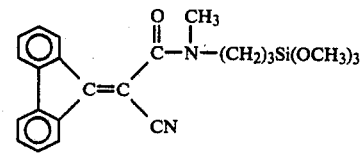

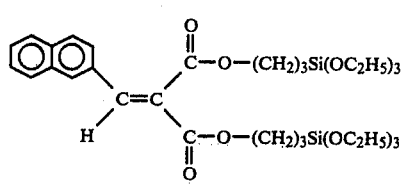

-continued

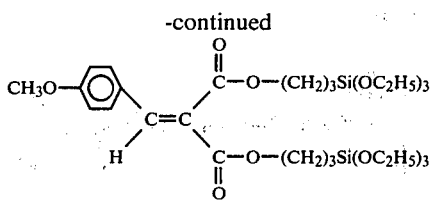

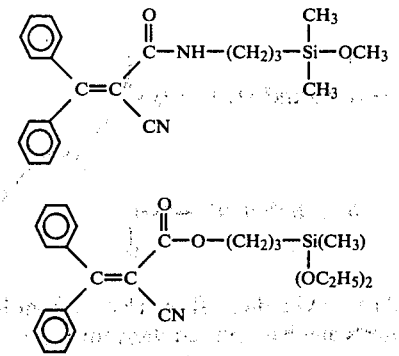

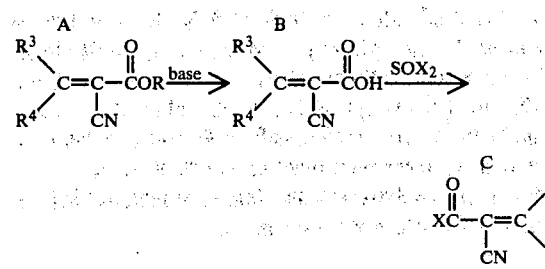

The alkoxysilanes of formula (1) can be made by effecting reaction between an aryl-substituted cyanoacrylic acid halide and an aminoalkyl silylalkoxysilane. Another procedure can involve the reaction between a hydroxyolefin and a cyanoacrylate followed by the hydrosilation of the resulting adduct. A further procedure is by the exchange between a cyanoacrylate ester and an alkoxyaminosilane in the presence of hydroxypyridene. A typical reaction, for example, is as follows, which involves the initial preparation of the corresponding acid chloride from the corresponding aryl-substituted cyanoacrylate:

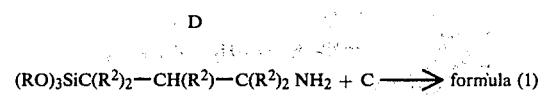

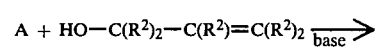

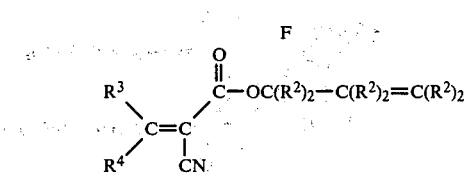

-continued

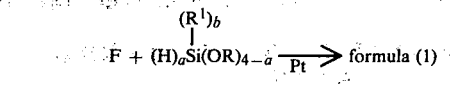

where X is a halogen radical and R, $R^1$, $R^2$, $R^3$ and $R^4$, a and b are as previously defined.

The silanes of formula 2 can be synthesized by a somewhat similar procedure, utilizing an aryl malonate derivative of the formula,

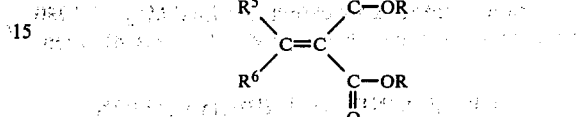

where R, $R^5$ and $R^6$ are as previously defined. Such silanes also can be prepared by direct ester alcohol and esteramide exchange.

In order that those skilled in the art will be better able practice the invention, the following examples are given by way of illustration and not by way of limitation. All parts are by weight.

EXAMPLE 1

There was added 18 parts of a 50% aqueous sodium hydroxide solution to about 55 parts of $\beta,\beta$-diphenyl-$\alpha$-cyanoethylacrylate dissolved in about 200 parts of a 25% aqueous methanol solution. The solution was stirred at room temperature for about 8 hours. After it was washed with ether, the aqueous solution was then neutralized with dilute hydrochloric acid resulting in the precipitation of product. There was obtained 48 parts, or a 97% yield of product having a melting point of 207°–209° C. Based on method of preparation, the product was $\beta,\beta$-diphenyl-$\alpha$-cyanoacrylic acid.

There was added 30 parts of thionyl chloride to a toluene solution of 50 parts of the $\beta,\beta$-diphenyl-$\alpha$-cyanoacrylic acid in about 100 parts of toluene. The mixture was refluxed for about 8 hours and then allowed to cool. There was obtained 49.5 parts of a product having a melting point of 157°–158° C. Based on method of preparation the product was $\beta,\beta$-diphenyl-$\alpha$-cyanoacrylic chloride.

There was added 2.67 parts of the above acrylic chloride in a tetrahydroforan solution of 2.21 parts of $\gamma$-aminopropyltriethoxysilane and 1.01 part of triethylamine, and the resulting solution was stirred at room temperature for 30 minutes. The resulting mixture was filtered off triethylamine hydrochloride salt and hexane was added to the filtrate, which resulted in the precipitation of product. There was obtained an 88.5% yield of product having a M.P. of 103.5°–104° C. Based on method of preparation, the product was (3-triethoxy silane propyl)-$\beta,\beta$-diphenyl-$\alpha$-cyanoacryl amide. The identity of the product was further confirmed by NMR and elemental analysis for CHN: C 66.4 (66.34), H 7.5 (7.13), N 6.3 (6.19).

EXAMPLE 2

There was added 9.5 parts of 2-hydroxypyridene to a mixture of 27.6 parts of the ethylester of $\beta,\beta$-diphenyl-$\alpha$-cyanoacrylic acid and 22.1 parts of $\gamma$-aminopropyltriethoxysilane. A mixture was heated at 150° C. for 4 hours. After the mixture cooled to ambient temperatures, it was washed with water and extracted with diethylether. After drying, the diethylether was evaporated resulting in a dark brown solid. The solid was recrystallized from an ether hexane solvent to provide 13 parts of 3-triethoxysilane propyl(β,β-diphenyl-α-cyano acrylamide). Its identity was confirmed by its M.P. 103°–104° C. and its NMR analysis which was identical to the product obtained in Example 1.

EXAMPLE 3

There was added 85 parts of allyl alcohol to a mixture of 27.6 parts of the ethylester of β,β-diphenyl-α-cyanoacrylic acid and 0.3 part of sodium methylate. The mixture was refluxed for 8 hours and all of the excess allyl alcohol was allowed to distill off. The resulting mixture was then washed with a 5% hydrochloric acid solution, a 5% sodium bicarbonate solution extracted with methylene chloride and dried. Upon evaporation of the organic solvent, there was obtained a light yellow oil. The oil gradually crystallized to form a colorless crystalline product. Based on method of preparation and NMR data, the product was allyl β,β-diphenyl-α-cyanoacrylate.

There was added 8.4 parts of triethoxysilane to 14.4 parts of the above allyl-β,β-diphenyl-α-cyanoacrylate and 0.02% by weight of a platinum catalyst prepared in accordance with the procedure of Karstead U.S. Pat. No. 3,715,334. The mixture was heated to 60° C. for 1 hour. There was obtained 12.95 parts of product obtained through a florisal column eluded with a 1:1 pentane/toluene mixture as solvent in the form of a light yellowish oil. Based on method of preparation and its NMR spectra the product was (3-triethoxysilane-propyl)-β,β-diphenyl-α-cyanoacrylate.

EXAMPLE 4

There is added 0.3 parts of sodium methoxide to a mixture of 21.8 parts of dimethylbenzylidene malonate and 60 parts of allyl alcohol. The resulting mixture is refluxed for 5 hours followed by distilling off the excess allyl alcohol and methanol. The resulting solution is washed with 5% aqueous hydrochloric acid, 5% aqueous sodium bicarbonate, water and extracted with methylene chloride upon evaporation of the solvent, there is obtained a viscous oil. Based on the method of preparation and NMR data, the product is diallyl benzylidene malonate.

There is added 16.5 parts of triethoxysilane to 13.5 parts of the above diallyl benzylidene malonate and 0.03% by weight of a platinum catalyst described above. The mixture is heated to 60° C. for 1 hour. There is obtained a quantitative viscous liquid. Column chromatography over florisal with 4:1 pentane/ether results in a light yellow liquid. Based on the method of preparation and its NMR spectra, the product is di(3-triethoxysilane)propyl benzylidene malonate.

EXAMPLE 5

There is added 22.1 parts by weight of Ludox LS silica Sol (Dupont, an aqueous dispersion of colloidal silica having an average paticle size of 12 milimicrons and a pH of 8.2) to a solution of 0.1 part by weight of methyltriacetoxysilane, and 26.8 parts by weight of methyltrimethoxysilane. The temperature of the reaction mixture is kept at 20°–25° C. The hydrolysis is allowed to continue for 24 hours. Five parts by weight of a polysiloxane-polyether copolymer (SF-1066) General Electric Company, is included as a flow control agent. The resulting cohydrolyzate has a solids content of 45%. Isobutanol is added to bring the solids content to 20%. The pH of the composition is about 7.2.

A composition is prepared by mixing 76 parts of the cohydrolyzate and 1.5 parts of (3-triethoxysilane-propyl)-β,β-diphenyl-α-cyanoacrylate. The resulting mixture is flow coated onto a 6 inch × 8 inch transparent Lexan polycarbonate panel which has been primed with a thermosetting acrylic emulsion. The treated panel is allowed to air dry for 30 minutes and then cured at 120° C. for 1 hour. After 500 Taber abraser cycles (500 gram loads, CS-10F wheels) according to ANIS-Z26.1-1977 section 5.17, the change in percent haze is found to be about 5.7. A similar sample is found to pass the cross-hatch adhesion test (DIN-35-151) after seven days immersion in water at 65° C.

Although the above examples are directed to only a few of the very many variables within the scope of the present invention, it should be understood that the present invention is directed to a much broader variety of alkoxysilylacrylamides, alkoxysilylacrylates and alkoxysilylbenzylidene malonates as shown by formula (1) and to organic thermoplastic substrates, for example, polycarbonate, polyesters, polyphenylene oxides, polyesterimides, etc. In addition to the coating compositions described in the above Example 2, there also can be employed in combination with about 0.8 to 4 parts by weight of the alkoxysilylacrylamide, alkoxysilylacrylate or alkoxysilylbenzylidene malonate of the present invention, 100 parts dispersion of colloidal silica in an aliphatic alcohol-water solution of the partial condensate of a silanol having the formula, $$R^7Si(OH)_3,$$

where $R^7$ is selected from the group consisting of $C_{(1-8)}$ alkyl and $C_{(6-13)}$ aryl, at least 70% by weight of the silanol being $CH_3Si(OH)_3$, where the dispersion contains from 10 to 50% by weight of solids, said solids consisting essentially of 10 to 70% by weight of colloidal silica and from 70 to 90% by weight of partial condensate and the dispersion has a pH of from 6.6 to 7.8, or 3.8 to 5.7.

What I claim as new and desire to secure by Letters Patent of the United States is:

1. Alkoxysilylacrylamides or alkoxysilylacrylates having the formula,

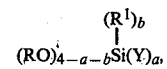

and alkoxysilylmalonates having the formula,

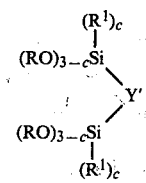

where Y is $$-C(R^2)_2CHR^2-C(R^2)_2-Q-\overset{O}{\underset{\|}{C}}-\underset{CN}{\overset{R^3}{\underset{|}{C}}}=C\overset{R^3}{\underset{R^4}{\diagdown}}$$

and Y'is $$-C(R^2)_2CHR^2-C(R^2)_2-Q-\overset{O}{\underset{\|}{C}}\diagdown_{C=C\diagdown_{R^6}^{R^5}}$$
$$-C(R^2)_2CHR^2-C(R^2)_2-Q-\underset{\|}{\overset{}{C}}\diagup$$
$$\phantom{-C(R^2)_2CHR^2-C(R^2)_2-Q-}O$$

R is a $C_{(1-8)}$ alkyl radical, $R^1$ is selected from R, $C_{(6-13)}$ aryl radicals and halogenated derivatives thereof, $R^2$ is selected from hydrogen and R radicals, $R^3$ and $R^5$ are selected from $C_{(6-13)}$ aryl radicals, $R^4$ and $R^6$ are selected from hydrogen, R and $R^3$ radicals, Q is selected from —O— and $$-\underset{R^2}{\overset{}{N}}-,$$

a is an integer equal to 1 to 3 inclusive, b is a whole number equal to 0 to 2 inclusive and c is a whole number equal to 0 to 2 inclusive and the sum of a+b is equal to 1 to 3 inclusive.

2. The compound (3-triethoxysilanepropyl)-$\beta,\beta$-diphenyl-$\alpha$-cyanoacryl amide.

3. The compound (3-triethoxysilanepropyl)-$\beta,\beta$-diphenyl-$\alpha$-cyanoacrylate.

4. A benzylidene malonate compound having the formula, $$CH_3O-\underset{}{\underset{}{\bigcirc}}\diagdown_{C=C\diagdown_{\overset{\|}{\underset{O}{C}}-O(CH_2)_3Si(OC_2H_5)_3}^{\overset{O}{\underset{\|}{C}}-O(CH_2)_3Si(OC_2H_5)_3}}$$

5. A method for making an alkoxysilane of the formula, $$(RO)_{4-a-b}\underset{\underset{(R^1)_b}{|}}{Si}(Y)_a,$$

which comprises,
(1) hydrolyzing a cyanoacrylate of the formula, $$\underset{R^4}{\overset{R_3}{\diagdown}}C=\underset{CN}{\overset{}{\underset{|}{C}}}-\overset{O}{\underset{\|}{C}}OR$$

in the presence of base,
(2) converting the resulting cyanoacrylic acid to the corresponding acid halide, (3) effecting reaction between the resulting acrylic acid halide and an aminoalkyl alkoxysialne of the formula, $$(RO)_3SiC(R^2)_2-CH(R^2)-C(R^2)_2\ NH_2+C,$$

where R is $C_{(1-8)}$ alkyl radical, $R^1$ is selected from R, $C_{(6-13)}$ aryl radicals and halogenated derivatives thereof, $R^2$ is selected from hydrogen and R radicals, $R^3$ is selected from $C_{(6-13)}$ aryl radicals, $R^4$ is selected from hydrogen, R and $R^3$ radicals, Y is $$-C(R^2)_2CHR^2-C(R^2)_2-Q-\overset{O}{\underset{\|}{C}}-\underset{CN}{\overset{R^3}{\underset{|}{C}}}-C\diagdown_{R^4}^{R^3},$$

Q is selected from —O— and $$-\underset{R^2}{\overset{}{N}}-,$$

a is an integer equal to 1 to 3 inclusive, b is a whole number equal to 0 to 2 inclusive and the sum of a+b is equal to 1 to 3 inclusive.

6. A method for making alkoxysilanes of the formula, $$(RO)_{4-a-b}\underset{\underset{(R^1)_b}{|}}{Si}(Y)_a,$$

which comprises,
(1) effecting reaction in the presence of base between a cyanoacrylate of the formula, $$\underset{R^4}{\overset{R_3}{\diagdown}}C=\underset{CN}{\overset{}{\underset{|}{C}}}-\overset{O}{\underset{\|}{C}}OR,$$

and an allyl alcohol of the formula, $$HO-C(R^2)_2-C(R^2)=C(R^2)_2,$$

(2) and effecting reaction between the resulting adduct of (1) and an alkoxysilane of the formula, $$(H)_a\underset{\underset{(R^1)_b}{|}}{Si}(OR)_{4-a},$$

in the presence of effective amount of platinum catalyst, where R is a $C_{(1-8)}$ alkyl radical, $R^1$ is selected from R, $C_{(6-13)}$ aryl radicals and halogenated derivatives thereof, $R^3$ is selected from $C_{(6-13)}$ aryl radicals, $R^4$ is selected from hydrogen, R and $R^3$ radicals, Y is $$-C(R^2)_2CHR^2-C(R^2)_2-Q-\overset{O}{\underset{\|}{C}}-\underset{CN}{\overset{}{\underset{|}{C}}}=C\diagdown_{R^4}^{R^3}$$

Q is selected from —O— and

a is an integer equal to 1 to 3 inclusive, b is a whole number equal to 0 to 2 inclusive and the sum of a+b is equal to 1 to 3 inclusive.

7. A method for making alkoxysilanes of the formula,

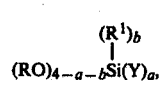

which comprises effecting reaction between an alkoxyaminosilane of the formula, $(RO)_3SiC(R^2)_2—CH(R^2)—C(R^2)_2 NH_2,$ and a cyanoacrylate ester of the formula,

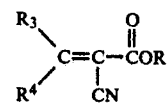

in the presence of hydroxypyridene, where R is a $C_{(1-8)}$ alkyl radical, $R^1$ is selected from R, $C_{(6-13)}$ aryl radicals and hydrogenated drivatives thereof, $R^2$ is selected from hydrogen and R radicals, $R^3$ is selected from $C_{(6-13)}$ aryl radicals, $R^4$ is selected from hydrogen, R and $R^3$ radicals, Y is

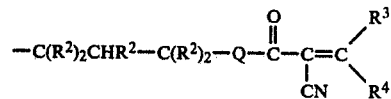

Q is selected from —O— and $-\underset{R^2}{\underset{|}{N}}-,$ a is an integer equal to 1 to 3 inclusive, b is a whole number equal to 0 to 2 inclusive and the sum of a+b is equal to 1 to 3 inclusive.

* * * * *